United States Patent [19]
Lisziewicz

[11] Patent Number: 6,130,089
[45] Date of Patent: Oct. 10, 2000

[54] MATERIALS AND METHODS FOR GENE TRANSFER

[76] Inventor: Julianna Lisziewicz, 4400 East-West Highway, Bethesda, Md. 20814

[21] Appl. No.: 08/989,301

[22] Filed: Dec. 11, 1997

Related U.S. Application Data

[60] Provisional application No. 60/032,826, Dec. 12, 1996.

[51] Int. Cl.[7] ............. C12N 15/87; C12N 15/86; C12N 15/88; C12N 5/00
[52] U.S. Cl. .............. 435/455; 435/456; 435/458; 435/325
[58] Field of Search ............... 435/172.1, 172.2, 435/172.3, 325, 240.2, 240.4, 320.1, 326, 327, 328, 329, 331, 334, 335, 336, 455, 456, 458; 424/450; 935/52, 54, 56, 57, 33, 34, 36, 38, 42; 514/43

[56] References Cited

U.S. PATENT DOCUMENTS 5,512,295  4/1996  Kornberg et al. ............... 424/450

OTHER PUBLICATIONS

Gao et al. Proc. natl. Acad. Sci. USA (1993) 90: 8925–8. Oct. 1993.

Meyerhans et al. J. Virology, (1994) 68(1):535–40. Jan. 1994.

*Primary Examiner*—Jon P. Weber
*Attorney, Agent, or Firm*—Valerie E. Looper

[57] ABSTRACT

The subject invention provides methods for improving the efficiency of gene transfer to a target cell. The methods are particularly advantageous in that they facilitate the transduction of quiescent cells. In a preferred embodiment the efficiency of gene transfer using a viral vector is enhanced by transiently loading the dytosol of the target cell with dNTP and by transiently adding viral receptors to the surface of the target cell.

8 Claims, 5 Drawing Sheets

(1 of 5 Drawing Sheet(s) Filed in Color)

MATERIALS AND METHODS FOR GENE TRANSFER

This application claim benefit of U.S. provisional application Ser. No. 60,032,826 filed Dec. 12, 1996.

BACKGROUND OF THE INVENTION

Deoxynucleotide triphosphates (dNTPs) are the natural raw materials for, or substrates of, viral and cellular polymerases, and reverse transcriptases. In the absence of dNTP, cells and viruses cannot synthesize their genetic materials and, consequently, cell division and/or virus replication is blocked. Sufficient quantities of dNTP must be available at the time of DNA synthesis if DNA replication or reverse transcription is to take place.

Ribonucleotide reductase (RR) is the sole enzyme responsible for the synthesis of dNTP. Without RR, dNTP production is slowed or completely eliminated, because the salvage of dNTP from cellular DNA represents only a minor, insignificant source of dNTP. It has been recognized for some time that hydroxyurea (HU) inhibits cellular, bacterial, and viral RR. HU as well as other RR-inhibitors have been used as antiviral and anticancer drugs (Cory, J. G. [1988] *Adv. Enzyme Regul.* 27:437–455). HU was also recently shown to block the replication of HIV by the same mechanism which limits the substrate (dNTP) for viral reverse transcriptase (Lori, et al. [1994] *Science* 266:801–805).

Cellular RR is a highly regulated enzyme. It consists of two dissimilar subunits M1 and M21 which are independently regulated during cell division. In cells resting in G0–G1 (no cellular DNA synthesis), cellular RR activity is diminished. Therefore, neither DNA nor RNA viruses can efficiently synthesize DNA in such quiescent cells. Some viruses, such as herpes simplex virus (HSV), pseudorabies, and Varicella-Zoster Virus (VZV), however, carry RR in their genome. These viral RR catalyze the same reaction as the mammalian enzyme, but the viral enzyme is free from allosteric regulation. Consequently, large pools of dNTP are created for viral DNA synthesis. Therefore, these viruses are able to productively replicate not only in dividing cells but also in quiescent cells even through such cells do not produce dNTP.

Typically, retroviruses can only infect dividing cells because dividing cells have sufficient amounts of dNTP available to support reverse transcription, while non-dividing cells have insufficient amounts of this substrate. The only known exceptions are the lentiretoviruses (e.g., HIV-1 and SIV). Some virus variants infect terminally differentiated cells, e.g. macrophages (MF). MF have higher levels of dNTP which are sufficient from macrophage tropic HIV or SIV variants to reverse transcribe their RNA genome (Gao et al. [1993] *PNAS* 90:8923–8928). However, these viruses do not replicate in quiescent lymphocytes because of incomplete reverse transcription of the viral RNA to DNA.

Retrovirus vectors are candidates for foreign gene delivery and have been evaluated for use in gene therapy approaches. Retrovirus vectors can permanently modify cells by integrating a foreign gene into the genome of a target cell. Retrovirus vectors are also advantageous because they are generally safe; therefore, they have already been approved for experimental gene therapy.

There are two major problems hindering the successful use of retrovirus vectors in gene therapy: the low efficiency of gene transfer and the incompetence to transduce non-dividing (quiescent) cells. Recent improvements of retrovirus vectros include the design of vectors with an extended host range (based, for example, on vesicular somatitis viruses instead of murine leukemia viruses) (Bums et al. *PNAS* 90:8033–8037), vectors which use multiple receptors for entry (Miller and Chen [1996] *J. Virol.* 70:5564–5571), vectors that are resistant to human serum (Cosset et al. [1995]*J. Virol* 69:7430–7436), and vectors which target new surface proteins (Somia et al. [1995] *PNAS* 92:7570–7574). Chu T. H. et al. [1994] *Gene Therapy* 1 (5):292–299) constructed a chimeric virus envelope of retrovirus vector with an antigen binding site of an antibody. Nilson et al. (Nilson, B. H. et al. [1996] *Gene Therapy* 3(4):280–286) exploited protease-substrate interaction for viral targeting. They fused epidermal growth factor (EGF) to a retroviral envelope and showed binding and gene transfer into cells expressing an EGF-receptor.

Lieber et al. ([1995] *Hum. Gene Ther.* 6:5–11) reported that adenovirus-mediated transfer of the amphotropic retrovirus receptor cDNA increased retroviral transduction in cultured cells. Adenovirus-mediated gene transfer results in permanent modification of cells not only with the viral-receptor gene but also with several adenovirus-vector genes. Introduction of undesired new genes into cells for the purpose of increasing the transfer of a therapeutic gene is highly undesirable and may be dangerous in gene therapy. Curiel et al. (Cold Spring Harbor Gene Therapy Meeting 1996, p. 158) reported using adenovirus vectors for gene delivery. They accomplished cell specific gene delivery by modifying the tropism of adenoviruses by introduction of ligands into the viral-vector envelope. Similarly, the coat protein of adenovirus vector particles were modified by other investigators to increase the entry in different cell types (Curiel et al., supra, p. 159).

All of the above approaches address transfer of genes into dividing cells. None of the presently known retrovirus vectors transduce quiescent cells. Naldini et al. [1996] *Science* 272:263–267) considered the use of a lentiretrovirus, HIV-1, as a gene delivery vehicle into non-dividing, quiescent cells. The HIV-based vector was able to deliver the lac-Z gene into growth-arrested cells. However, this approach did not result in integration and gene expression in growth-arrested cells.

BRIEF SUMMARY OF THE INVENTION

The present invention concerns materials and methods for increasing the efficiency of gene transfer and integration of a foreign gene into dividing and non-dividing (quiescent) cells. Advantageously, the materials and methods of the subject invention make it possible to efficiently transduce quiescent cells with a desired foreign gene.

The methods of the subject invention comprise transduction of cells of a human or animal host with a construct cloned into a virus vector. Preferably, the virus vector is replication deficient. In a preferred embodiment of the subject invention, the target cell membrane is transiently modified with the receptor of the virus vector and is contemporaneously transiently loaded with deoxynucleotide triphosphates (dNTP) which are the building blocks of DNA. The virus-receptor on the surface of the target cells facilitates efficient entry of the virus vector into the cell. Moreover, the dNTP in the cytosol of the target cell serves as a substrate for the DNA synthesis of the virus vector transducing the target cell.

One specific embodiment of the subject invention concerns the transduction of cells with constructs cloned into retrovirus vectors including Murine Moloney Leukemia Virus-based arnphotropic retrovirus vectors. These vectors have been used for experimental gene therapy. Increasing the number of amphotropic-receptor molecules (phosphate transporters) on the surface of the cells increases the entry of a replication defective virus vector and also allows the transduction of cells which do not express receptor molecules. Increasing the amount of dNTP in the cytosol of the cells decreases or eliminates the degradation of retrovirus RNA inside the cells by stimulation of the reverse transcription of viral RNA to DNA. The fully reverse-transcribed DNA is then able to integrate into the chromosomes of the target cells independently of the state of cell division.

In a preferred embodiment, the advantages of the subject invention are achieved by transient modification of the target cell membrane by insertion of virus' receptor protein. Consequently, any viral vector can be used in any cell type independently of the tropism of the virus. Thus, the subject invention circumvents the problem of the tropism and specificity of viral vectors to transduce cells expressing receptors of the virus.

There are several applications where permanent gene transfer (integration of a gene) into non-dividing cells is required. Such applications include, for example, gene transfer into hematopoiectic stem cells, neurons, muscle cells, liver cells, and epithelial cells. The gene transfer technology of the subject invention can be used to improve retrovirus vector gene delivery for ex vivo and in vivo gene therapy for infectious diseases, cancer, and genetic diseases.

Pursuant to the teachings of the present invention, in a preferred embodiment, the efficiency of transduction by virus vectors can be increased significantly in the presence of a viral receptor on the membrane and the dNTP in the cytosol of target cells. Agents increasing the intracellular dNTP concentration induce viral DNA synthesis and retroviral reverse transcription, integration, gene expression and replication. It has been found that, advantageously, a transient increase of dNTP concentration in the cells is not toxic.

BRIEF SUMMARY OF THE DRAWINGS

The file of this patent contains at least one drawing executed in color. Copies of this patent with color drawings (s) will be provided by the Patent and Trademark Office upon request and payment of the necessary fee.

DETAILED DISCLOSURE OF THE INVENTION

The present invention concerns materials and methods for increasing the efficiency of gene transfer and integration of a foreign gene into a recipient cell. Thus the teachings provided herein have applicability in the field of gene therapy.

The teachings of the present invention are particularly advantageous because they facilitate gene transfer into both dividing and non-dividing (quiescent cells). In a preferred embodiment of the subject invention, target cells which are to be transduced with a foreign gene are transiently loaded with viral receptors on the surface and with dNTP in the cytosol contemporaneously with transduction by a viral vector. Increasing the receptor and dNTP concentration as described herein results in increased efficiency of gene delivery.

Figure 1:
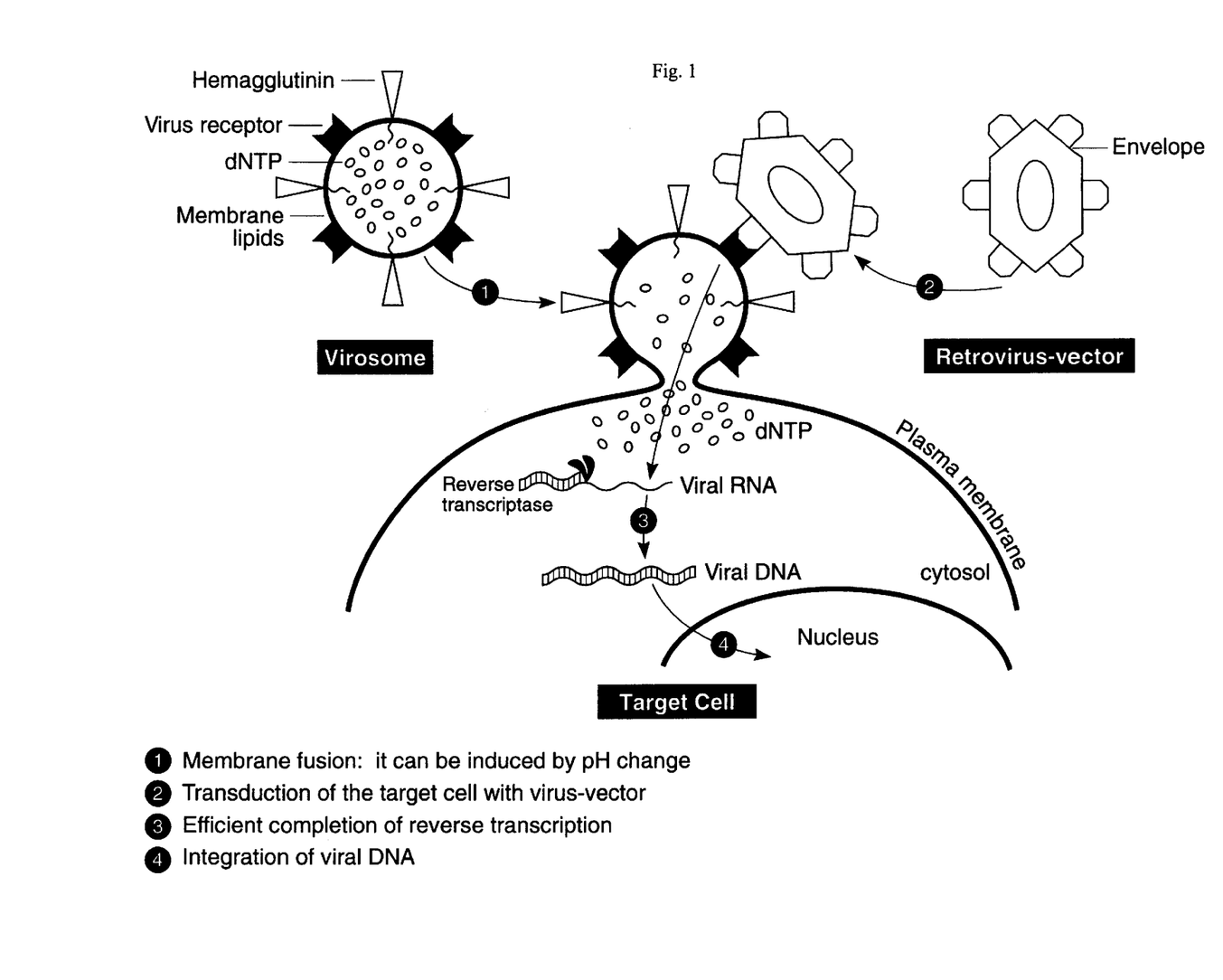
FIG. 1 shows a preferred embodiment of the subject invention.

In a preferred embodiment, the methods of the subject invention comprise transduction of cells of a human or animal host with a construct cloned into a virus vector. In a preferred embodiment, the virus vector is replication deficient. According to the subject invention, the membrane of the target cell in transiently loaded with membrane proteins which serve as receptors for the viral vector. Transient introduction of a protein into the target cell membrane is particularly advantageous because it is metabilized by the cells; therefore, it cannot permanently influence the function of the cell and its progeny. Increasing the amount of receptor protein on the cells in accordance with the subject invention increases the entry of the viral vector. A preferred embodiment of the subject invention is depicted in FIG. 1. FIG. 1 shows a virosome loaded with dNTP and having virus receptors and hemagglutinin at its surface, bind with and release its dNTP contents into a target cell. FIG. 1 also shows a retrovirus vector binding to the virus receptor on the virosome at the surface of the target cell. The viral RNA then enters the target cell and, after reverse transcription, viral DNA enters the nucleus of the target cell.

In a specific embodiment of the subject invention, increased dNTP in the cytosol of quiescent cells results in efficient gene transfer with a retrovirus vector. Since gene expression after retrovirus vector gene delivery requires integration of the foreign gene, dNTP delivery into the target cells not only effects reverse transcription, but also allows integration of the foreign gene.

The practice of the subject invention is particularly advantageous because it results in an improvement of the efficiency of gene transfer compared to the currently used MMLV based vectors, or other retro- or lentivirus vector systems. Also, unlike current systems, it is possible to achieve transduction and integration of a foreign gene carried by a virus vector into quiescent cells.

Transient Modification of the Membrane of the Target Cells

In a preferred embodiment, the methods of the subject invention comprise transduction of cells of a human or animal host with a construct cloned into a virus vector. Viral vectors are efficient tools to introduce genes into vertebrate cells. However, their use is limited by the host range of the virus from which they derived. Several methods have been developed to alter or extend the host range of the vector particle. However, in contrast to modifying the tropism of the virus, one aspect of the subject invention involves transiently modifying the target cells in order to increase the efficiency and the specificity of viral entry and, consequently, virus-mediated gene transfer.

According to the subject invention, the membrane of the target cell can be transiently loaded with membrane proteins which serve as receptors of the viral vector. Increasing the amount of receptor protein on the cells in accordance with the subject invention increased the entry of the viral vector. Alternatively, if the target cell does not contain viral receptors in the membrane, it can have a new protein placed on the surface of the cell. This new protein serves as a receptor of the virus vector and facilitates the viral entry.

Fusogenic particles such as virosomes, liposomes, and microvesicles are able to merge with the cell membrane and establish a continuity between their interiors. After fusion, the fusogenic particle membrane becomes part of the cell membrane. This mechanism can be exploited to introduce new molecules into the target cell membrane. Thus, to render cells highly susceptible to virus infection, the receptor of the virus can be introduced into the membrane of the target cell.

Advantageously, using membrane fusion to introduce molecules in the target cell membrane does not necessarily result in undesired permanent modification of the cell. Transient introduction of a protein into the target cell membrane is safe because it is metabilized by the cells; therefore, it cannot permanently influence the function of the cell and its progeny.

Loading Target Cells With dNTP

Following viral entry, introduction of a foreign gene into cells with virus vectors requires DNA synthesis in the target cells. The precursor of viral and cellular DNA synthesis is dNTP, the production of which, by the cellular-RR, is limited in quiescent cells. Retrovirus vectors can enter into several different quiescent cells but do not transduce these cells because there are not sufficient amounts of dNTP for DNA synthesis.

The methods of the subject invention comprise transduction of cells of a human or animal host with a construct cloned into a virus vector. According to the subject invention, the target cell is transiently loaded with dNTP. Increasing the concentration of dNTP in the cells in accordance with the teachings of the subject invention results in the efficient completion of DNA synthesis.

In the particular case of retrovirus vectors, dNTP in the target cells serves as the substrate of the reverse transcriptase of the retrovirus vector transducing the target cell. Increasing the amount of dNTP in cells in accordance with the subject invention decreases or eliminates the degradation of retrovirus RNA inside the cells by stimulation of the reverse transcription of viral RNA to DNA. The fully reverse-transcribed DNA is then able to integrate into the chromosomes of the target cells independently of the state of cell division.

Fusogenic Particle for Transient Modification of Target Cells

In a preferred embodiment of the subject invention, the amount of dNTP in the target cells can be increased by loading dNTP into the cells utilizing particles which are able to encapsulate small molecules such as dNTP and deliver these molecules directly into the cytosol. In a preferred embodiment, the delivery vehicle can be a liposome (El Barka et al. [1996] *Biochim. Biophys. Acta* 1280:107–114; Goni et al. [1994] *Biochem. Soc. Trans.* 22:839–844, microvesicles ([1995] *Neurochem. Int.* 27:219–226), or a virosome (Wybenga et al. [1996] *Biochemistry* 35:9513–9519; Moesby et al. [1995] *Biochemistry* 33:10319–10324) which is able to efficiently encapsulate dNTP and inject the dNTP into the cytosol after either the membrane fusion or receptor mediated endocytosis.

Incubation of cells with free dNTP can be toxic for the cell. However, increasing the amount of cytoplasmic dNTP by direct delivery using a liposome, virosome, or microvesicle according to the subject invention is non-toxic for the cell and is also transient because cells rapidly metabolize these natural compounds.

The liposomes, virosomes, microvesicles, or other delivery vehicle used to deliver the dNTP according to the subject invention can be prepared in any of a variety of ways which are known to those skilled in the art. In a preferred embodiment, the vesicle carrying the dNTP will be fusogenic so as to facilitate transfer of the dNTP directly from the vesicle into the target cell. Methods for producing such vesicles are known to those skilled in the art and include, for example, PCT application WO 92/06677 which describes a double detergent dialysis procedure for making stable unilamellar vesicles suitable for encapsulating and delivering dNTP.

In a particularly preferred embodiment, the liposomes, vesicles, or virosomes used to deliver the dNTP may have embedded within their membrane, one or more molecules. These molecules serve to direct the liposome to the target cell; synthesize dNTP in the target cell; and/or direct the viral vector to a cell which has been transiently loaded with dNTP. In one embodiment the delivery vehicle may have embedded on its surface, proteins which bind to receptors on the surface of the target cell, thus directing the vehicle to that cell. In another embodiment, the delivery vehicle may have embedded on its surface a transmembrane ribonucleotide reductase (Smith et al. [1996] *Virology* 217:425–4340), which can catalyze dNTP synthesis in the target cells. In another embodiment, the delivery vehicle may have a receptor for the viral vector. Once the delivery vehicle has fused with the target cell, and emptied its content (e.g., dNTP) into the cell, the delivery vehicle remains associated with the cell surface. Thus, by including a receptor for the viral vector or RR in the delivery vehicle, this receptor becomes likewise associated with the cell surface thus assisting in the targeting of the viral vector to the dNTP-loaded cell.

In a preferred embodiment, the target cells are transduced with a retrovirus vector simultaneously or shortly after injection of dNTP. Transduction should occur before there is substantial degradation of the surface viral receptor and cytosolic-dNTP which has been loaded into the cell.

Modification of viral vectors.

In one embodiment of the subject invention, the dNTP concentration in the target cells can be increased by incorporating an enzyme into the virus particle. Preferably, the enzyme can be a ribonucleotide reductase (RR) or an activator of cellular RR. RR is the sole enzyme responsible for the synthesis of dNTP. The RR can be of either cellular or viral origin. Since cells resistant to HU express high amounts of the R2 subunit, expression of this subunit may be sufficient to activate the cellular RR. The advantage of using viral RR is the absence of allosteric regulation. Herpes virus RR localizes on the cell surface and is internalized by the endocytic pathway.

In one embodiment of the subject invention, viralRR, or an activator of cellular RR, can be incorporated into the virus-vector particles after expression of these proteins in the packaging cell line. For example, a gene encoding a viral RR can be cloned at the 3' end of a gag gene connecting the RR gene with a sequence encoding a protease cleavage site. In this embodiment, the RR, together with the gag protein, is transported into the membrane where the virus is budding. In the bud, the viral protease cleaves the free enzyme (ribonucleotide reductase) similarly to the other gag encoded proteins and the RR incorporates together with other viral proteins into the retrovirus particle.

In one embodiment of the subject invention, retrovirus-producing cell lines can be altered with genes encoding a viral RR High dNTP concentration in the producer cell line stimulates the reverse transcription during the budding of the virus and inside the virus particle. The RR gene can be introduced by standard procedures into packaging cell lines. Preferably, the RR gene can be introduced with other genes encoding the structural proteins of the retrovirus. Alternatively, replication defective retrovirus vectors can be produced by a packaging line transfected with a high copy number of episomal vectors (Hofman, A. et al., *Proc. Natl. Acad. Sci.* 93:5185–5190) which produce the packageable RNA encoding a foreign gene. Thus, in a specific embodiment, the vectors used according to the subject invention can be modified to include a viral or cellular RR driven by a strong promoter in the episomal vector outside of the retrovirus transcriptional unit. This results in high levels of expression of RR and production of dNTP will be ensured in all cells with the episomal vector and producing packageable RNA. This vector can contain a puromycin selection marker outside of the retroviral transcriptional unit.

Another way to increase reverse transcription and integration into quiescent cells is to incorporate into a retrovirus vector particle a mutant reverse transcriptase instead of the wild type version. The mutant reverse transcriptase should be able to efficiently reverse transcribe the RNA genome in the presence of low levels of dNTP. There are several methods for selection of such a mutant RT. For example, standard methods of in vitro mutagenesis and enzymatic assays can be utilized. In a preferred embodiment, however, in vivo selection is used. For example, HIV-1 infected patients treated with a hydroxyurea and ddI combination typically respond to the treatment because HIV RT cannot efficiently utilize low levels of dNTP. However, if a patient responds poorly to the treatment, the viral RT may be mutated so as to be able to utilize low levels of dNTP present in the hydroxyurea treated cells. The RT can be cloned from plasma or from the isolated lymphocytes of such a patient. Efficiency of reverse transcription in the presence of low levels of dNTP can be confirmed and also compared with other RTs. Then, site directed mutagenesis to mimic the mutation in the RT can be performed and a retrovirus vector packaging line can be modified with the mutant RT. Alternatively, the mutant HIV RT can be used instead of the wild type RT present in the packaging cell line. Consequently, the RT which is able to utilize low levels of dNTPs will be carried by the virus particle. After infection the mutant RT will allow reverse transcription of the retrovirus vector RNA to proceed in the presence of low amounts of dNTP.

In order to stimulate cell division and/or cellular RR, the SIV or HIV nef gene can also be incorporated into the retrovirus particle. Nef can be inserted in the envelope or the gag gene and processed by a protease or an independent transcriptional unit. However, to avoid potential toxicity, retrovirus vectors should not carry genes encoding any of these proteins. Genetic modification of the cells with genes able to permanently change the level of dNTP may interfere with the normal function of the cells in contrast to the short term transient increase of dNTP as described herein.

In a specific embodiment of the subject invention, reverse transcription can be stimulated prior to transduction to produce more stable viral particles containing not only RNA, but also partially synthesized DNA. This can be achieved by the published method by Zhang and coworkers ([1995] *J. Virol.* 69:3929–3932) of incubating the free virus particles with dNTP, which results in partial DNA transcription in the virion and a higher efficiency of transduction.

The dNTP injection technique can also be used with virus vectors other than retroviruses, because an increased amount of dNTP will also increase the virulence of DNA virus vectors, where DNA synthesis is required (e.g.,alpha herpes viruses which are also proposed for gene therapy use).

Gene Transfer Procedures

The methods of subject invention can be used for both ex vivo gene transfer and also in vivo gene therapy.

In one embodiment of the subject invention, the virus vector can be injected together with the fusogenic particles into the brain, bone marrow, liver or any other tissue. In a preferred embodiment, the fusogenic particles (described above) carry the receptor of the viral vector and dNTP. Fusion between a pH-sensitive fusogenic particle and the target cells in vivo may be initiated with a short pH change. Fusion results in insertion of the viral receptor into the cell membrane and injection of the dNTP. The virus vector can utilize the newly inserted receptor for entry and the dNTP for DNA synthesis. In a preferred embodiment, retrovirus vectors with envelopes resistant to human complement can be injected or infused into the patient.

In accordance with the teachings of the subject invention, retrovirus vectors can be used to deliver and integrate genes effectively in both quiescent and activated cells by increasing the concentration of dNTP in the recipient cells. This feature is extremely important in gene therapy using quiescent cells as the target because partially reverse transcribed RNA-DNA complexes can be eliminated by cellular enzymes if the cells do not undergo cell division in a short period of time. However, it is also true that a partially reverse transcribed RNA-DNA complex is more stable than RNA alone. In the case of HIV-based vectors, this stability results in efficient reverse transcription, integration, and gene expression in dividing cells, macrophages, or neurons where the amount of dNTP substrate is sufficient to complete reverse transcription.

The subject invention can be readily utilized in gene therapy. It can be used in combination with gene delivery systems in any application which utilizes virus vectors, including retro- and lentivirus vectors. In addition, the invention is useful to study, for example, hematopoiesis, because activation of cells during the gene transfer, which induces differentiation, can be avoided. The techniques described herein can also be used in gene therapy to deliver an antiviral gene into quiescent lymphoid cells, neurons, liver cells, epithelial cells, fibroblasts and stem cells.

Increasing the concentration of dNTP in the cytosol of cells increases the efficiency of gene transfer and gene expression in both quiescent and activated cells.

Following are examples which illustrate procedures for practicing the invention. These examples should not be construed as limiting.

EXAMPLE 1

Gene Transfer into Growth-Arrested Cells

A replication defective Moloney Murine Retrovirus Vector carrying a lac-Z gene was used. Retrovirus vector supernatant was generated following standard procedures and NIH 3T3 cells were used to test the efficiency of gene transfer in the presence and absence of cytosomal dNTP. Cells transduced with lac-Z containing retrovirus vectors express beta-galactosidase which can be detected by an in situ staining procedure. After staining, retrovirally-transduced cells stained blue in contrast to non-transduced cells.

NIH3T3 cells were plated at varying densities. At high density, cell proliferation is known to be blocked. However, at medium and low density, cells can divide until confluence. Aliquots of these cells were treated with dNTP by induction of membrane fusion by acidic pH. Virosomes were prepared in the presence of 2.9 mM dATP, 14.3 mM dCTP, 7.1 mM dGTP, and 17.9 mM dTTP. The ratios of these amounts correspond roughly to the ratios of the differences in dNTP levels between quiescent and PHA-stimulated PALS (Gao et al. [1993] *PNAS* 90:8923–8928). After dNTP treatment, cells were transduced with retrovirus vector supernatant. Beta-galactosidase expression was measured 2 days after transduction by histochemical staining. Results of these experiments are shown in Table 1.

TABLE 1

| CELL DENSITY (NIH 3T3) | PRESENCE OF dNTP % TRANSDUCED CELLS | ABSENCE OF dNTP % TRANSDUCED CELLS |
| --- | --- | --- |
| Confluent | 27.3 | 1.2 |
| Medium | 25.5 | 4.3 |
| Low | 40.7 | 6.6 |

Figure 2:
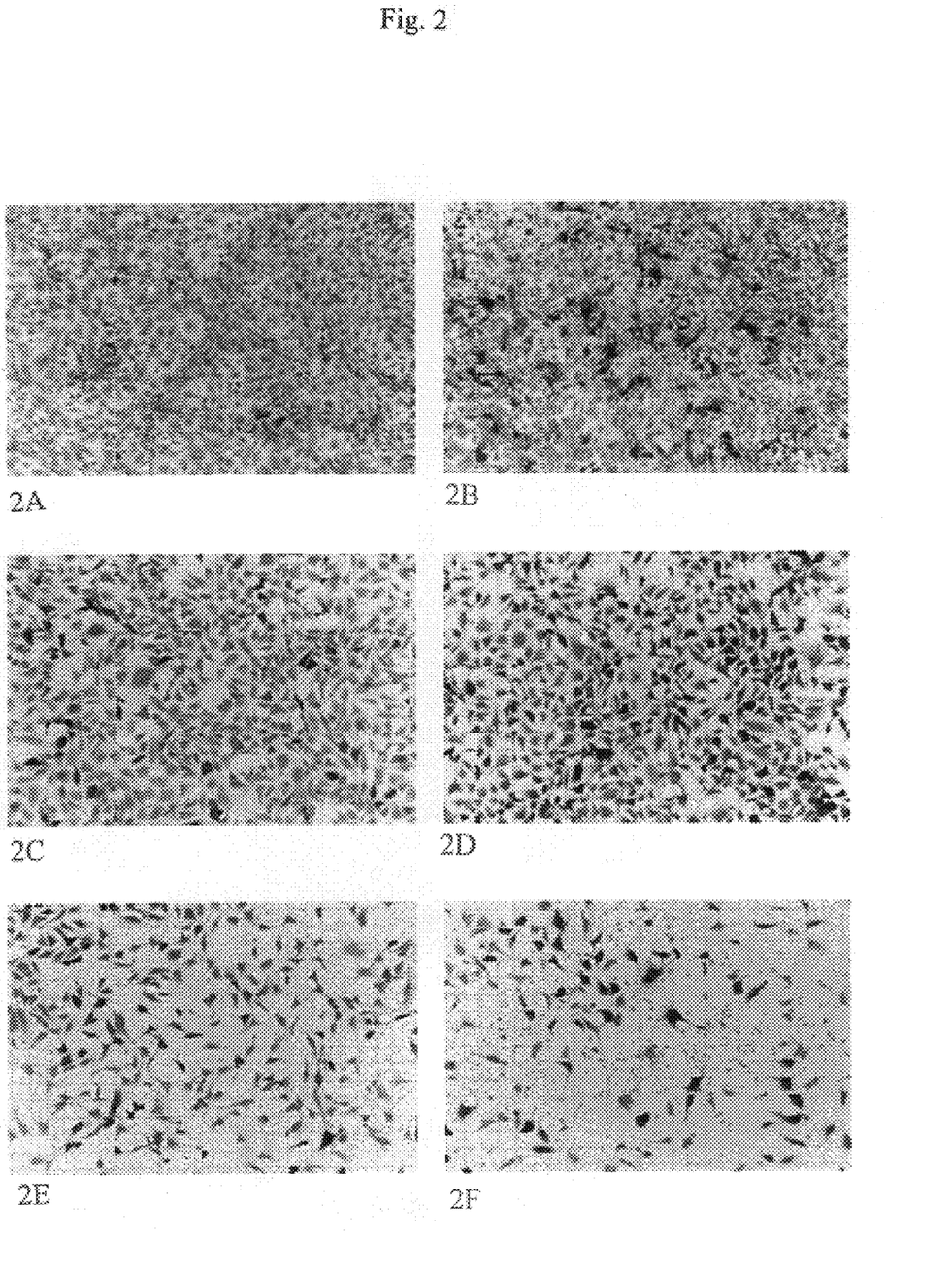
FIGS. 2A–2F show the transduction of cells with a retrovirus vector comprising a Lac-Z gene.

The results of these experiments are also shown in FIGS. 2A–2F. FIG. 2A shows confluent NIH 3T3 cells transduced with a Lac-Z containing retrovirus vector. FIG. 2B is the same as FIG. 2A except that the cells were treated with a virosome containing dNTP. FIG. 2C shows dividing NIH 3T3 cells transduced with Lac-Z containing retrovirus vector. FIG. 2D is the same as FIG. 2C except that the cells were treated with a virosome containing dNTP. FIG. 2E shows single NIH 3T3 cells transduced with Lac-Z containing retrovirus vector. FIG. 2F is the same as FIG. 2E except that the cells were treated with a virosome containing dNTP. Blue cells are the transduced beta-galactosidase expressing cells. The results of these experiments demonstrate that dNTP-injection into the target cells increases the transduction efficiency of retroviral vectors in both quiescent and dividing cells.

These results demonstrate that cells containing dNTPs can be efficiently transduced with retrovirus vectors compared with cells which do not contain dNTP. This procedure is particularly advantageous because of the significantly increased efficiency of gene transfer into growth arrested cells. This is demonstrated by the confluent cell density results.

EXAMPLE 2

Gene Transfer Into Quiescent Lymphocytes

Aliquots of quiescent lymphocytes were treated with dNTP-containing virosomes and membrane fusion was induced by acidification according to a published protocol (Bron et al. [1993] *Methods Enzymol.* 220:313–33; Bron et al. [1994] *Biochemistry* 33:9110–9117). Following dNTP injection, dNTP-containing and control (no dNTP) cells were infected with HIV-1. Virus replication was only detected in the supernatant of cells treated with dNTP. The control quiescent lymphocytes containing no extra dNTP did not replicate HIV-1 (FIG. 3).

Figure 3A:
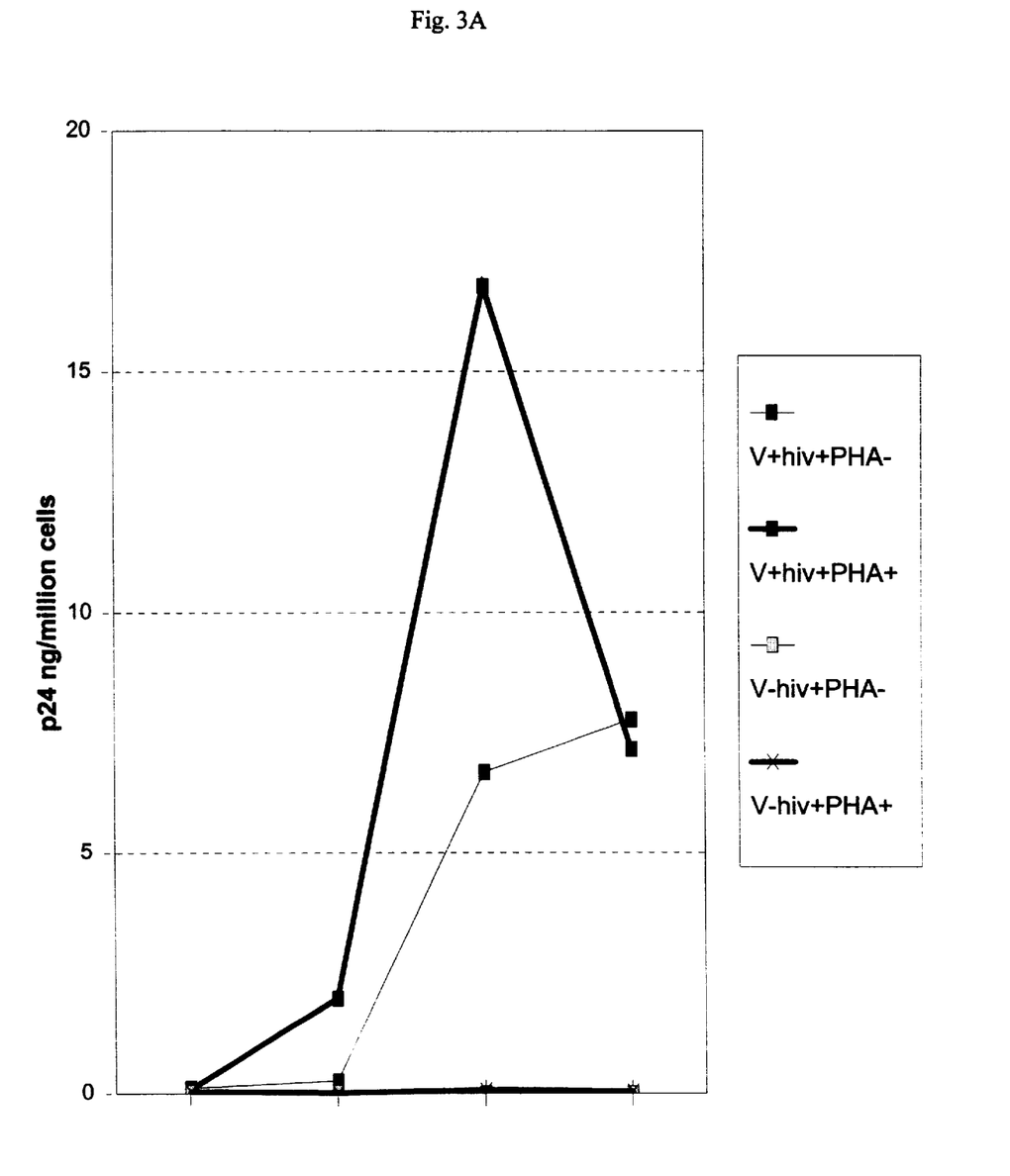
FIGS. 3A–3C show the results of transduction experiments carried out on quiescent peripheral blood lymphocytes.
Figure 3B:
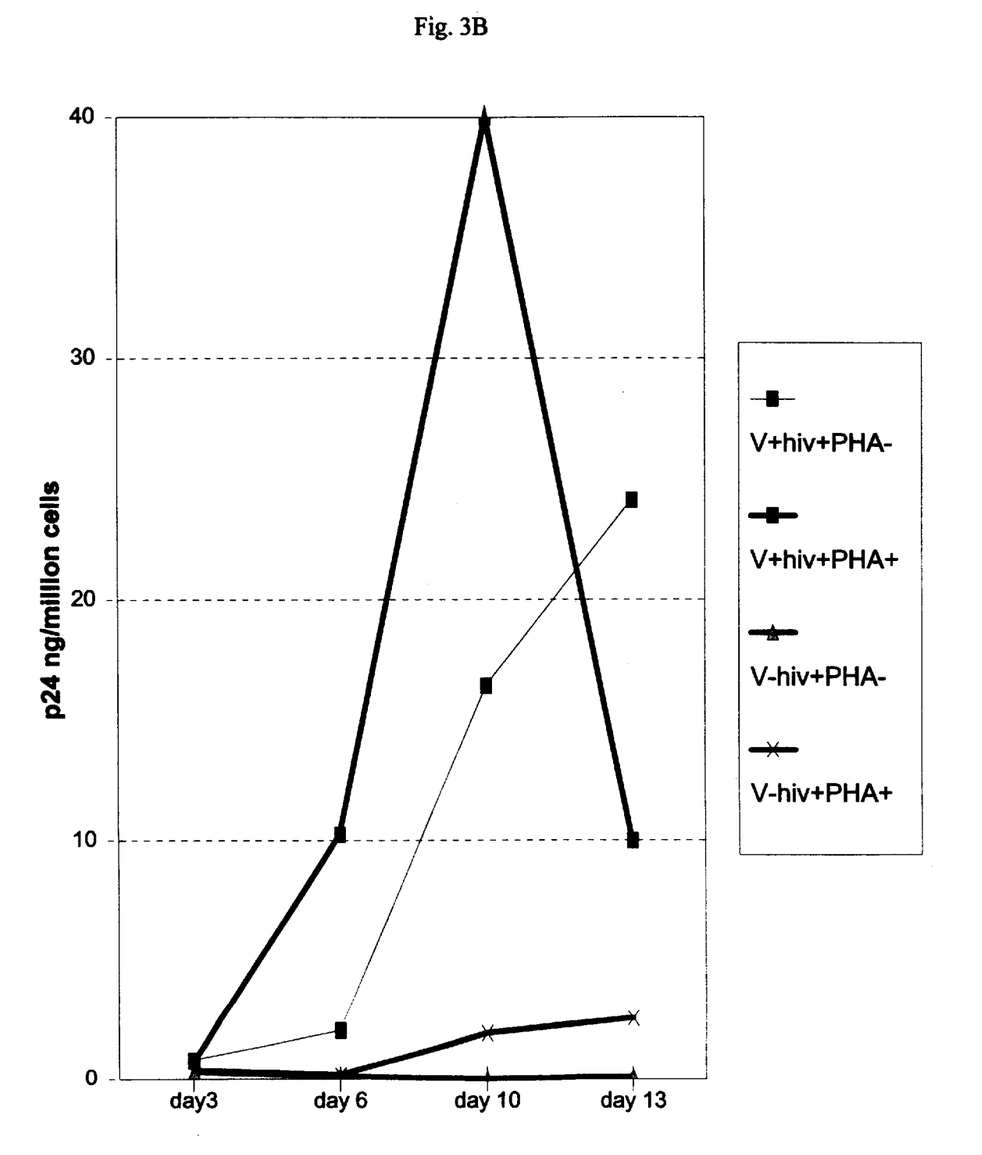
Figure 3C:
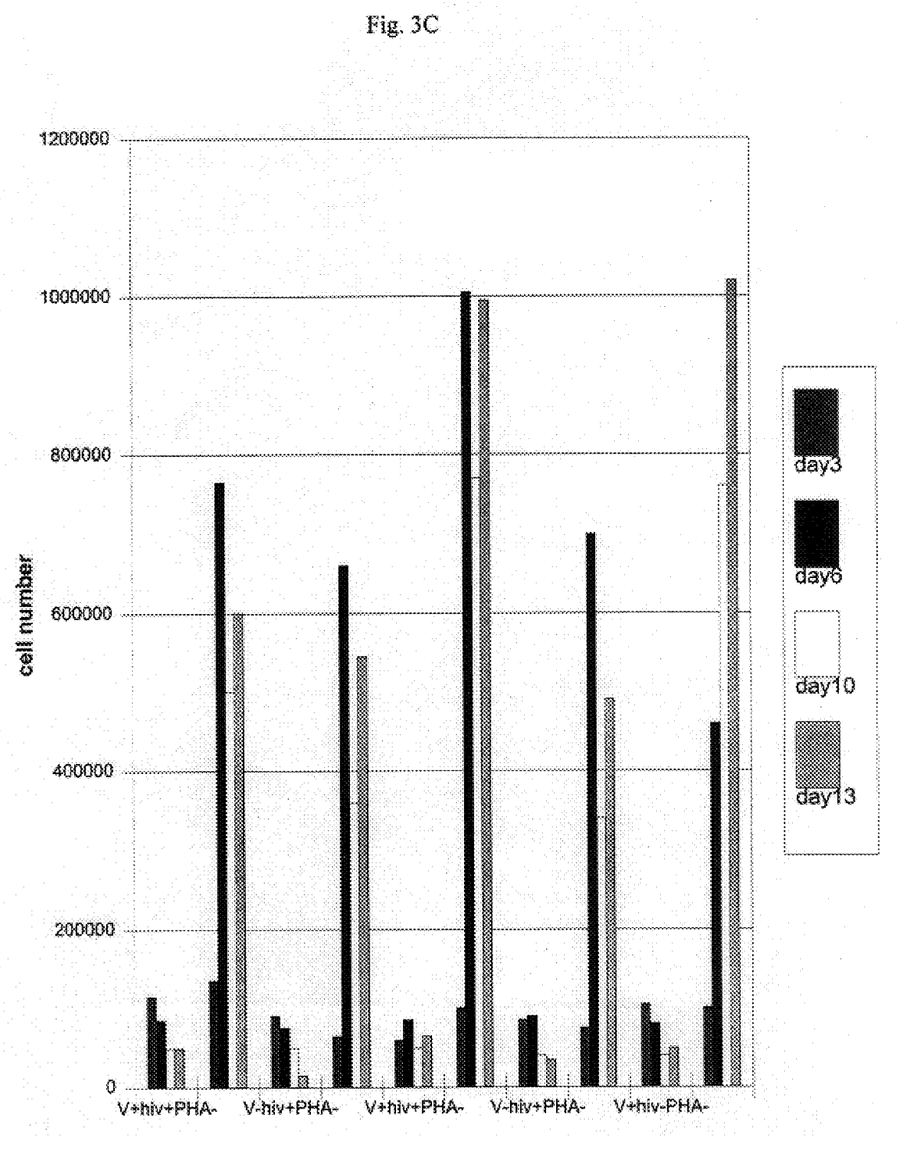

FIGS. 3A, 3B and 3C demonstrate the results of experiments carried out on quiescent peripheral blood lymphocytes (PBL). PBL were isolated from normal donors and cultured in RPMI 1640 complemented with 10% FCS according to standard procedures. Aliquots of cells were treated with dNTP-containing virosomes to inject dNTP(V+ label) untreated aliquots were used as a control (V-label). After treatment, both aliquots were infected with HIV-1 (HTLV-I/IIIB). Following HIV-1 infection, part of the cells were activated by phytohemagglutinin (PHA).

Two different multiplicities of infection (MOI) are indicated in FIG. 3. HIV-1 replication was monitored in the supernatant by p24 antigen capture assay (Coulter), and the cell number was counted. FIGS. 3A and 3B depict HIV-1 replication after infection with MOI 0.0001 and MOI 0.001. Quiescent cells created with dNTP (V+HIV+PHA–)and activated cells treated with dNTP (V+HIV+PHA) produce the virus similarly in contrast to infected cells which were not treated with dNTPs (V–HIV+PHA+) and (V–HIV+PHA–). At low MOI (A=0.0001) cells not containing additional dNTP(V–) do not produce significant amount of virus in contrast to higher MOI (B=0.001) where activated cells are able to express a significant amount of virus even in the absence of dNTP (V–HIV+PHA–). FIG. 3C depicts the cell number during the course of the experiment to prove that quiescent cells indeed did not divide compared with the PHA-activated ones.

It is also known from the literature (Zhand et al. [1996] *J. Virol.* 70:2809–2824) that infected quiescent lymphocytes stimulated to cell division after infection replicate the virus (see data above: MOI=0.001; V–HIV+PHA+). These results correspond with the feature of the HIV-1-based gene delivery vector, where integration and gene expression can be detected after induction of cell division following gene transfer (Naldini et al. [1996] *Science* 272:263–267).

These results demonstrate the ability to achieve gene transfer with lentiretrovirus vectors (e.g., HIV-based) including the completion of reverse transcription and integration in the absence of stimulated cell division.

EXAMPLE 3

Gene Transfer Into Peripheral Blood Cells

Presently, protocols exist for retrovirus mediated gene transfer into lymphocytes utilizing simulation and expansion of T-cells. In vitro stimulation and expansion of lymphocytes, however, can lead to transformation and/or loss of immunological function. In addition, bulk expansion of CD4+ cells is not expected to reconstitute the immune system of patients suffering HIV invection.

The current invention allows retrovirus vector-mediated transfer of an antiviral gene into quiescent cells and therefore cells without in vitro immunological stimulation can be reintroduced back to the patient. Mononuclear cells isolated from patients can be treated with virosomes. Short acidification of the media following neutralization can be used to facilitate membrane fusion. Membrane fusion inserts the amphotropic-receptor into the lymphocytes' membrane and loads the cells with dNTP. Then, cells can be transduced with retrovirus vectors carrying an antiviral gene. Transduction may be repeated several times. Alternatively, after virosome treatment, cells can be seeded into a filter and retrovirus supernatant can be poured over allowing the supernatant flow through the filter. This procedure results in increased contact between the virus vector and the target cells. For HIV gene therapy, it is preferable for the retrovirus vector not express any proteins, not even the selection marker (i.e., the neomycin phosphotransferase gene) to avoid presentation of the foreign gene and destruction of the protected cells by cytotoxic T-lymphocytes. In the case of higher efficiency gene transfer, selection is not required.

It has been determined that cells infected with HIV can be transduced more readily with an amphotrophic retrovirus vector than can uninfected cells. One reason may be that HIV-1 carries a protein which is a cofactor of cellular ribonucleotide reductase. Consequently, HIV-1 infected cells may contain more dNTP than uninfected cells which results in increased reverse transcription and gene expression. Transduced cells can be reintroduced into a patient to achieve in vivo expansion. If T-cell turnover is as fast as was recently predicted (Ho et al. ][1995] *Nature* 373:123–126; Wei et al [1995] *Nature* 373:117–122), protected cells have a selective growth advantage and will expand faster than unprotected cells. However, ex vivo gene therapy allows only the treatment of some portion of the total peripheral cells and also the lifetime of lymphocytes is limited. Therefore, repeated genetic treatment is preferred.

EXAMPLE 4

Gene Transfer Into Hematopoietic Stem Cells

The major advantage of stem cell therapy is that successful gene transfer into hematopoietic stem cells can result in repopulating of the hematopoietic system with genetically modified cells. Stem cell gene therapy can be utilized in all cases where bone marrow transplantation can be an effective treatment including, for example, in several genetic diseases, viral infections, and hematopoietic cancers. Specifically, HIV infection can be treated with stem-cell gene therapy. Stem and progenitor cells in HIV infection can be treated with stem-cell gene therapy. Stem and progenitor cells in HIV invection can be modified with an antiviral gene which renders them and all of the progeny resistant to virus replication. It was recently predicted (Ho et al. [1995] Nature 373:123–126; Wei et al. [1995] Nature 373:117–122, 1995) that T cell turnover in HIV infected individuals is very high (less than 3 days half life). If this mathematical prediction is true, protected cells will have a selective growth advantage and they will repopulate the hematopoietic system.

Stem cell gene transfer can be carried out ex vivo, where bone marrow or cord blood is collected, and treated with a fusogenic particle containing virus-receptors and dNTP as described above. These cells can be transduced with a retrovirus vector carrying an antiviral gene. The vectors described above can be used. Important features of the antiviral gene include the regulated expression of the antiviral RNA, absence of any protein expression, and highly efficient antiviral activity. Following transduction, the cells can be injected back into the patient.

Similarly, the invention can be utilized for in vivo gene transfer. Bone marrow may be collected to give space for biological and genetic manipulations. Fusogenic particles containing virus-receptors and dNTP can be injected and, if required, followed by a short acidification to allow membrane fusion. After this, virus-vector can be injected to transfer the foreign gene(s) into bone marrow cells. Retrovirus vectors are preferably injected as virus vectors or irradiated retrovirus-vectors producer cells can also be injected. Alternatively, the fusogenic particles can be injected together with the retrovirus vector particle. Genetically modified stem cells will then differentiate in vivo and the resistant progeny will repopulate the hematopoietic system.

EXAMPLE 5

Utilization of the Invention in Cancer Gene Therapy

Cancers, like AML, neuroblastoma and lymphoma can be treated by genetically modified bone marrow cells. These treatments can utilize the technology of the subject invention by using autologous genetically modified stem cell transplantation. Stem cells and/or other bone marrow cells transduced with antitumor genes (e.g., expression of tumor suppression gene p53) can be modified ex vivo or in vivo according to the subject invention.

EXAMPLE 6

Utilization of the Invention in Gene Therapy of Genetic Diseases

Adenosine deaminase deficiency (ADA) can be treated by retroviral mediated gene transfer. Using the invention, stem cells and peripheral blood cells can be treated as described in HIV gene therapy using retrovirus vectors containing the ADA gene. Other hematopoietic genetic disorders, for example, sickle cell anemia, Gaucher disease and thalassemia, can also be treated using the procedures described herein.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed:

1. A method for transferring a foreign polynucleotide carried by a viral vector to a recipient cell wherein said method comprises increasing the concentration of dNTP in the cytosol of said recipient cell at the time when said foreign poplynucleotide is effectively present in said cell by exposing the recipient cell to a dNTP delivery vehicle containing dNTPs wherein said vehicle is selected from the group consisting of virosomes, liposomes, and microvesicles.

2. The method, according to claim 1 wherein said delivery vehicle comprises a receptor for said viral vector such that said receptor becomes inserted into the membrane of said recipient cell as said dNTP is effectively delivered to the cytosol of said recipient cell.

3. The method, according to claim 1 wherein said delivery vehicle has, at its surface, molecules which target said delivery vehicle to said recipient cell.

4. The method, according to claim 1, wherein said recipient cell is a quiescent cell.

5. The method, according to claim 1, wherein said recipient cell is selected from the group consisting of hematopoietic stem cells, neurons, muscle cells, liver cells, and epithelial cells.

6. The method, according to claim 1, wherein said recipient cells are transformed ex vivo.

7. The method, according to claim 1, wherein said virus vector is replication deficient.

8. The method, according to claim 1, wherein said virus vector is a retrovirus vector.

* * * * *